United States Patent [19]
Svoboda et al.

[11] 3,975,161
[45] Aug. 17, 1976

[54] BIOLOGICAL DIAGNOSTIC TEST STRIP

[75] Inventors: Vlastimil Svoboda; Olga Celechovska, both of Brno, Czechoslovakia

[73] Assignee: Lachema, narodni podnik, Brno, Czechoslovakia

[22] Filed: Nov. 6, 1975

[21] Appl. No.: 629,690

[30] Foreign Application Priority Data
Feb. 14, 1975 Czechoslovakia .................... 972-75

[52] U.S. Cl. ................................. 23/253; 23/230 B
[51] Int. Cl.² .................. G01N 31/22; G01N 33/16
[58] Field of Search ..................... 23/253 TP, 230 B

[56] References Cited
UNITED STATES PATENTS

| | | | |
|---|---|---|---|
| 3,290,117 | 12/1966 | Adams, Jr. et al. | 23/230 B |
| 3,853,472 | 12/1974 | Rittersdorf et al. | 23/230 B |

*Primary Examiner*—Robert M. Reese

[57] ABSTRACT

Diagnostic test strips for the qualitative detection and semi-quantitative estimation of blood and hemoglobin in biological products include a reagent area comprising an organic hydroperoxide or salt thereof, a chromagen and a novel agent capable of accelerating the peroxidase activity of hemoglobin. The accelerating agent is an aromatic hydrocarbon of the general formula

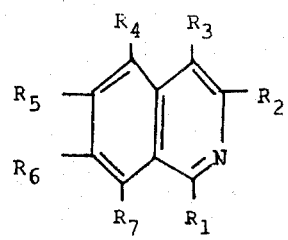

wherein $R_1 - R_7$ are hydrogen or alkyl or alkoxy groups having 1–2 carbon atoms. The resultant test strips evidence marked enhancement in sensitivity as compared with prior art materials.

9 Claims, No Drawings

BIOLOGICAL DIAGNOSTIC TEST STRIP

This invention relates to diagnostic test strips of the type disclosed in our copending application Ser. No. 622,833 filed Oct. 16, 1975. More particularly, the present invention relates to diagnostic test strips suitable for the qualitative detection and semi-quantitative estimation of blood and hemoglobin in biological products.

Chemical methods employed in clinical chemistry for the rapid detection and quantitative estimation of blood and hemoglobin in biological fluids and materials such as urine, gastric juices, vomitus, cerebrospinal fluid, feces and the like have been effected by the use of diagnostic test strips which take advantage of the pseudo peroxidase activity of hemoglobin. The strip employed for this purpose includes a test area which contains an organic peroxide, an acid buffer capable of maintaining the pH of the test area of the strip within the range of 3–7, a colorless chromogen capable of being oxidized to a colored product, a wetting agent and a film-forming material which is polymeric in nature. In use, the colorless chromogen is oxidized by the hydroperoxide to an intensely colored product, oxidation being initiated by the catalytic peroxidase action of hemoglobin.

Unfortunately, the diagnostic test strips presently being used commercially for such purposes evidence limited sensitivity and, consequently, only permit the detection of hemoglobin or erythrocytes in amounts which exceed clinical limitations. Accordingly, such limitation precludes the use of such strips for many diagnostic purposes. Additionally, the presence of certain compositions such as ascorbic acid, uric acid, gentisic acid, glutathione and the like tend to decrease the sensitivity of the test strip or even result in false negative results. Lastly, the aforementioned oxidation of the colorless chromogen to a colored oxidation product proceeds slowly, so necessitating evaluation over lengthy time periods.

Some years ago, workers in the art recognized that the peroxidase activity of hemoglobin could be enhanced by the presence of quinoline or derivatives thereof such as quinine (see British Pat. No. 1,057,056). Although sensitivity has, indeed, been enhanced by such techniques, the resultant sensitivity fails to meet diagnostic standards in many cases because it permits detection of blood or hemoglobin only in concentrations ranging from 100–200 erythrocytes per $\mu$l of urine, that is, at a dilution of 1:50,000 to 1:100,000.

Efforts to further enhance the sensitivity of these diagnostic test strips focused upon the use of quinoline derivatives in the benzo, dibenzo and pyridoquinoline families. Specific compositions found suitable for this purpose are phenanthridine, benzo-/F/-quinoline, p- or m-phenanthroline and the like. Although these compositions do, in fact, evidence better accelerating characteristics than the simple derivatives of quinoline, they still fail to meet clinical standards for detection of free hemoglobin or myoglobin present in urine in cases of hemoglobinuria, myoglobinuria and as a result of hemolysis of erythrocytes originally present. Still further, at low hemoglobin concentrations the reaction rate is too slow to permit rapid evaluation and the characteristic coloration relied upon as the calibrating tool is oftimes adversely affected.

In accordance with the present invention, the foregoing prior art limitations are successfully obviated by the use of a novel diagnostic test strip wherein the test or reagent area of the strip includes an accelerating agent having the general formula

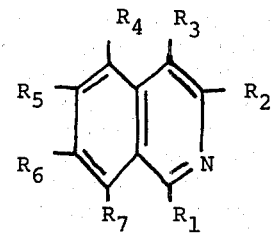

wherein $R_1 - R_7$ are selected from the group consisting of hydrogen, alkyl groups having from 1–2 carbon atoms and alkoxy groups having from 1–2 atoms. Compounds found to be of particular interest for this purpose are isoquinoline, 3-methylisoquinoline, 6-methoxy-isoquinoline and 3-methyl-6-methoxyisoquinoline. Studies have revealed that test strips including the foregoing compositions permit the detection of erythrocytes as brightly colored spots on the pale background of the strips and minute amounts of free hemoglobin equivalent to 3–5 erythrocytes per 1 $\mu$l of urine. An added benefit resides in the fact that test results may be monitored within 20–30 seconds after immersion in the fluid being tested.

It will be appreciated by those skilled in the art that the activity of the various accelerating agents employed in the practice of the present invention differ in activity depending upon location of substituents. Thus, for example, 3-methyl-isoquinoline evidences high activity as an accelerator whereas unsubstituted isoquinoline is less effective in the described environment. Selection of appropriate accelerators will therefore permit detection of traces of hemoglobin in the cerebrospinal fluid or in urine in anticoagulant medication control, thereby eliminating the laborious and time-consuming hematological techniques utilized heretofore for such purposes. Similarly, the less sensitive isoquinolines may be used for the preparation of test strips for evaluating occult bleeding into the stool.

The accelerating agents employed in the practice of the present invention are conveniently employed in the form of free bases or as a stable salt of an organic or inorganic acid, such as hydrochloric, sulfuric, oxalic and the like. It is preferable in the preparation of an impregnation solution containing a non-aqueous solvent such as benzene, toluene, chloroform and the like to use a free base as the accelerator whereas in the preparation of impregnation media containing an aqueous solvent, salts of the isoquinoline derivatives are employed. In either case, the accelerating agents are employed in an amount ranging from 0.05 – 2.5 grams per 100 ml of impregnation solution, a preferred range being 0.3 – 1.5 grams/100 ml of solution.

Other components in the test area of the novel diagnostic strips may be selected from among any of the well-known prior art materials employed for such purposes. Thus, the test area includes an organic hydroperoxide, an acid buffer capable of maintaining a pH in the test area within the range of 3–7, a chromogen, a wetting agent, and a solid, polymeric film-forming material or synthetic substance, the combined mixture being disposed upon an adsorbent bibulous carrier material.

Typical organic hydroperoxides suitable for use in the practice of the present invention are cumene hydroperoxide, 1,4-diisopropylbenzene-1,4-dihydroperoxide, 2,5-dimethylhexane-2,5-dihydroperoxide, 1-hydroxycyclohexane-1-hydroperoxide and p-methane-hydroperoxide and the like. The hydroperoxides may be protected in the reagent area either by encapsulation in microcapsules, as described in British Pat. No. 1,057,056, or by stabilization with phosphoric acid amides. Alternatively, the hydroperoxide may be employed in the form of a stable, solid, non-volatile salt of an aliphatic, alicyclic or heterocyclic amine or an aminoalcohol. The highest sensitivities are achieved by use of the phosphoric acid amide or amine salt hydroperoxide.

As indicated, the acid buffer selected must be capable of maintaining a pH in the test area within the range of 3-7. Typical of such buffers are mixtures of polyvalent organic or inorganic acids such as those in the citrate, tartrate, phosphate, phthalate or succinate families having a molarity ranging from 0.5 – 4.0.

The chromogen employed may be selected from among any known chromogen which is stable and undergoes a change in color in the presence of a hydroperoxide and blood or hemoglobin. Typical compositions found suitable for this purpose are o-tolidine benzidine, o-tolidine, o-dianisidine, 2,7-diaminofluorene, guaiacol and certain substituted azines. The chromogens are employed in an amount ranging from 0.05 – 5.0 grams/100 ml of impregnation solution, a general preference existing for 0.2 – 2.0 grams/100 ml of solution.

The wetting agent is an optional element which when present is found to enhance the absorptivity of the test area and hence the reaction rate. For this purpose, any of the well-known anionic, non-ionic or cationic detergents may be employed. A general preference has been found to exist for anionic detergents. Typical of such detergents are sodium laurylsulfate, sodium dodecylbenzene sulfonate, sodium dialkylsulfosuccinate, etc. The wetting agents are employed in an amount ranging from 0.1 – 0.5 grams/100 ml of impregnation solution with a preferred range being from 0.2 – 2.0 grams/100 ml of solution.

As indicated, the test area of the diagnostic strip may also include a polymeric, natural or synthetic film-forming organic substance which is capable of protecting the test area against the deleterious influence of ambient humidity and air and precluding premature impregnation of reagents during the preparative process. The organic substance employed must be water soluble, soluble in the solvent used for the preparation of the impregnation solution, incapable of participating in the oxidation reaction and following evaporation of the solvent must be capable of forming a partially water wettable film on the bibulous carrier. Materials meeting these requirements are sodium alginate, starch, gelatin, polyvinylalcohol, polyvinylpyrrolidone, carboxymethyl cellulose, polyethylene glycols and the like or mixtures of any of the foregoing.

Additionally, the reagent area of the strips may include hydroperoxide stabilizers such as the amides of phosphoric acid or organic amines, or chelating agents such as the heametaphosphates or organic complexes which suppress the occurrence of false positive results attributed to traces of heavy metal ions which are present as impurities in the bibulous carrier or in the chemicals used. Lastly, the reagent area may include a dye capable of correcting the color shade of the strips during negative or positive reactions.

In the preparation of the described test strips, it is desirable to separate the organic hydroperoxide from other ingredients. This end is attained by impregnating a bibulous carrier such as filter paper, cellulose fleece or felt derived from synthetic fibers with a first impregnant using water or an aqueous lower aliphatic ($C_1$ – $C_3$) alcohol as solvent for the chromogen, buffer and other ingredients and, subsequently, after thorough drying the resultant impregnated layer is overlaid with a solution of hydroperoxide in a non-aqueous solvent, such as benzene, toluene, chloroform, ethylene dichloride, ethyl acetate and the like. This procedure enables a total separation of the hydroperoxide from the other ingredients which may be added to the first impregnation solution, thereby enhancing the stability of the test strips.

Diagnostic test strips designed for detection of blood and hemoglobin in biological fluids and materials prepared in accordance with the present invention have been found superior to those of the prior art. More specifically, the described strips are capable of detecting erythrocytes or hemoglobin in water at a dilution of 1:6,000,000 to 1:7,000,000 and in urine at a dilution of 1:1,000,000 to 1:2,000,000 which corresponds with as few as 700–800 erythrocytes or an equivalent amount of hemoglobin in 1 ml of water and 2,500 – 5,000 erythrocytes in the same volume of urine. Furthermore, the strips permit the detection of certain microorganisms, molds or yeasts in urine, the cells of which form intense blue spots on the pale background of the strips. Accordingly, the novel diagnostic strips are eminently suited for detection of hematuria and hemoglobinuria as well as pathological conditions such as bacteriuria.

Several examples of the present invention are set forth below. It will be appreciated by those skilled in the art that these examples are set forth merely for purposes of exposition and are not to be construed as limiting.

EXAMPLE I

A carrier comprising filter paper was impregnated with two solutions as set forth below, each solution being applied independently and the impregnated carrier being thoroughly dried in hot air at a temperature within the range of 50°–60°C after each impregnation.

| Solution 1 | |
|---|---|
| o-tolidine hydrochloride | 4.0 grams |
| 3-methyl-isoquinoline | 4.2 grams |
| 5% solution of polyvinylpyrrolidone | 150.0 ml |
| 1.5 molar citrate buffer (pH 3.8) | 150.0 ml |

| Solution 2 | |
|---|---|
| Salt of cumene hydroperoxide with 1,4-diazabicyclo/2,2,2/-octane | 12.0 grams |
| 1,4-diazabicyclo/2,2,2/-octane | 15.0 grams |
| solid polyvinylpyrrolidone | 2.0 grams |
| 4% solution of polyvinylpyrrolidone in 2:1 toluene:ethanol | 300.0 ml |

The resultant impregnated paper was cut into narrow strips, 5 × 60 mm in size. Upon immersion of the cut strips in urine containing erythrocytes or hemoglobin, they turned an intense green or blue in color within a time range of 20–30 seconds, the coloration depending on the amount of hemoglobin present. Specific erythrocytes were found to form intense blue spots on the pale yellow background of the strips whereas free hemoglobin was found to turn the entirety of the immersed area into a uniformly colored mass. The presence of from 3–5 erythrocytes or an equivalent amount of free hemoglobin in 1 μl of urine was detected in this manner.

EXAMPLE 2

The procedure of Example 1 was repeated using the following solutions:

Solution 1

| | |
|---|---|
| o-tolidine hydrochloride | 4.0 grams |
| isoquinoline hydrochloride | 4.6 grams |
| polyvinylpyrrolidone | 7.5 grams |
| 2.0 molar citrate buffer (pH 3.8) | 100.0 ml |
| water | 300.0 ml |

Solution 2

| | |
|---|---|
| polyvinylpyrrolidone | 16.0 grams |
| triethylene diamine | 26.0 grams |
| cumine hydroperoxide (cca 80%) | 12.0 ml |
| sodium dioctylsulfosuccinate | 0.8 grams |
| ethanol | 140.0 ml |
| toluene | 280.0 ml |

The sensitivity of the resultant strips was approximately one-half that evidenced by the strips of Example 1.

EXAMPLE 3

The procedure of Example 1 was repeated using the following impregnation solutions:

Solution 1

| | |
|---|---|
| 1.2 molar citrate buffer (pH 5.25) | 35.0 ml |
| disodium ethylene diaminetetraacetate | 0.1 grams |
| sodium dioctylsulfosuccinate | 2.0 grams |
| 2,5-dimethylhexane-2,5-dihydroperoxide (cca 70%) | 1.6 grams |
| phosphoric acid trimorpholide | 12.7 grams |
| ethanol | 30.0 ml |
| water | 100.0 ml |

Solution 2

| | |
|---|---|
| o-tolidine | 0.3 grams |
| 3-methyl-6-methoxy-isoquinoline | 0.3 grams |
| toluene | 100.0 ml |

The sensitivity of the resultant strips was found to be comparable to that evidenced by the strips of Example 1.

What is claimed is:

1. Diagnostic test strip for the qualitative detection and the semi-quantitative estimation of blood and hemoglobin in biological materials comprising a bibulous carrier impregnated with a composition of matter comprising (a) an organic hydroperoxide or salt thereof, (b) an acid buffer, (c) a chromogen, (d) a wetting agent, (e) a solid polymeric film-forming natural or synthetic substance and (f) an agent capable of accelerating the peroxidase activity of hemoglobin characterized in that said agent is of the general formula

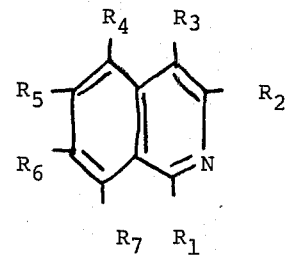

wherein $R_1 - R_7$ are selected from the group consisting of hydrogen, alkyl groups having from 1–2 carbon atoms and alkoxy groups having from 1–2 carbon atoms.

2. Diagnostic test strip in accordance with claim 1, wherein the accelerating agent is 3-methyl-isoquinoline.

3. Diagnostic test strip in accordance with claim 1, wherein the accelerating agent is isoquinoline hydrochloride.

4. Diagnostic test strip in accordance with claim 1, wherein the accelerating agent is 3-methyl-6-methoxyisoquinoline.

5. Diagnostic test strip in accordance with claim 1, wherein the bibulous carrier is filter paper.

6. Diagnostic test strip in accordance with claim 1, wherein the hydroperoxide is selected from the group consisting of cumene hydroperoxide, para-menthane-hydroperoxide, 1,4-diisopropylbenzene-1,4-dihydroperoxide, 2,5-dimethylhexane 2,5-dihydroperoxide, or 1-hydroxycyclohexane-1-hydroperoxide.

7. Diagnostic test strip in accordance with claim 6, wherein the acid buffer is capable of maintaining the pH in the strip within the range of 3–7.

8. Diagnostic test strip in accordance with claim 7, wherein the accelerating agent is employed in an amount ranging from 0.05 – 2.5 grams per 100 ml of impregnating composition.

9. Diagnostic test strip in accordance with claim 8, wherein the accelerating agent is employed in an amount ranging from 0.3 – 1.5 grams per 100 ml of impregnating composition.

* * * * *